United States Patent [19]

Short

[11] Patent Number: 5,342,011
[45] Date of Patent: Aug. 30, 1994

[54] FLUID CONTAINER ATTACHMENT ADAPTOR FOR AN AMBULATORY FLUID DELIVERY SYSTEM

[75] Inventor: Leland H. Short, Morrow, Ohio

[73] Assignee: Sherwood Medical Company, St. Louis, Mo.

[21] Appl. No.: 6,300

[22] Filed: Jan. 19, 1993

[51] Int. Cl.⁵ .............................................. A47H 1/10
[52] U.S. Cl. ..................... 248/318; 211/71; 248/121
[58] Field of Search ............... 248/318, 317, 121; 211/71, 113, 162, 107, 74, 117

[56] References Cited

U.S. PATENT DOCUMENTS

| | | | |
|---|---|---|---|
| 3,006,481 | 10/1961 | Gussack | 211/117 |
| 3,191,904 | 6/1965 | Kapapita | 211/117 X |
| 4,044,983 | 8/1977 | Francis | 248/318 |
| 4,047,687 | 9/1977 | Turner | 211/117 X |
| 4,289,244 | 9/1981 | Frankhouser | 248/318 X |
| 4,367,859 | 1/1983 | Lamon | 248/318 |
| 4,961,557 | 10/1990 | Garvin | 211/74 X |

FOREIGN PATENT DOCUMENTS 2523592 12/1976 Fed. Rep. of Germany ...... 248/318

*Primary Examiner*—J. Franklin Foss
*Attorney, Agent, or Firm*—Andrew J. Beck; Montgomery W. Smith; Gene B. Kartchner

[57] ABSTRACT

The present invention relates to a fluid container attachment adaptor for an ambulatory fluid delivery system which includes a support device for attachment of a fluid delivery set and a pump. The fluid container attachment adaptor allows simple attachment to the support device of fluid containers which have been designed for attachment to commonly used IV poles. The fluid container attachment adaptor preferably includes a disk-shaped body portion and a hook-shaped attachment member which is positioned centrally thereon, and extends away from the body portion. The disk-shaped body portion is designed to be accepted within the clamping members of the support device and the hook-shaped attachment member is designed to receive a fluid container for suspension from the adaptor in substantially the same manner as the fluid container may have been attached to a standard IV pole. The invention therefore adapts the support device so that it may be usable with several types of fluid containers which have been primarily designed for use with IV poles.

3 Claims, 6 Drawing Sheets

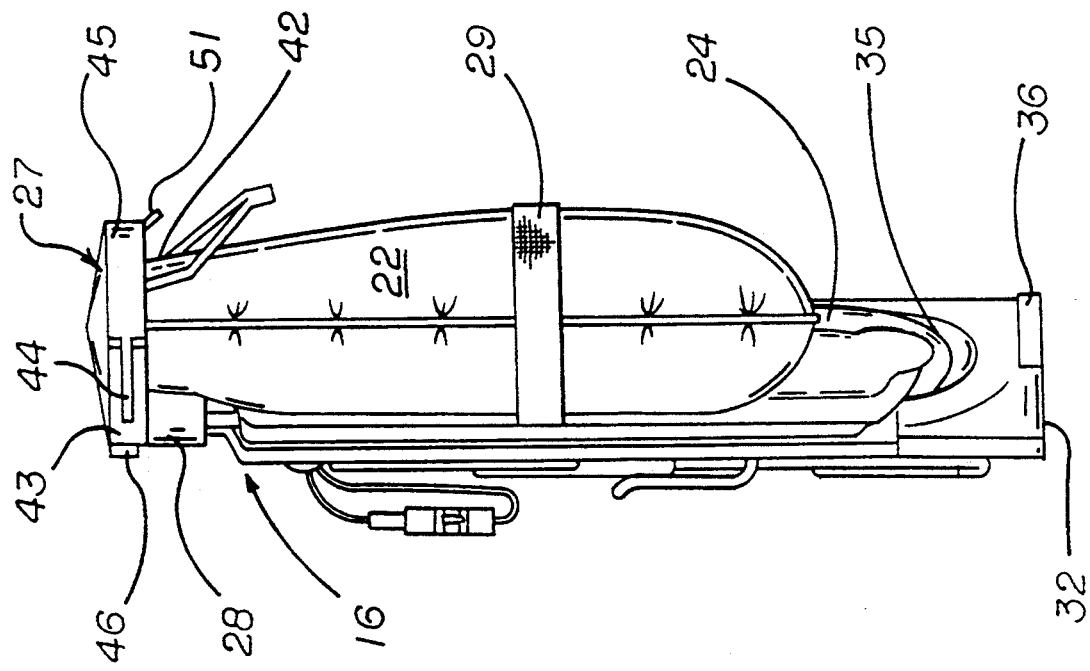
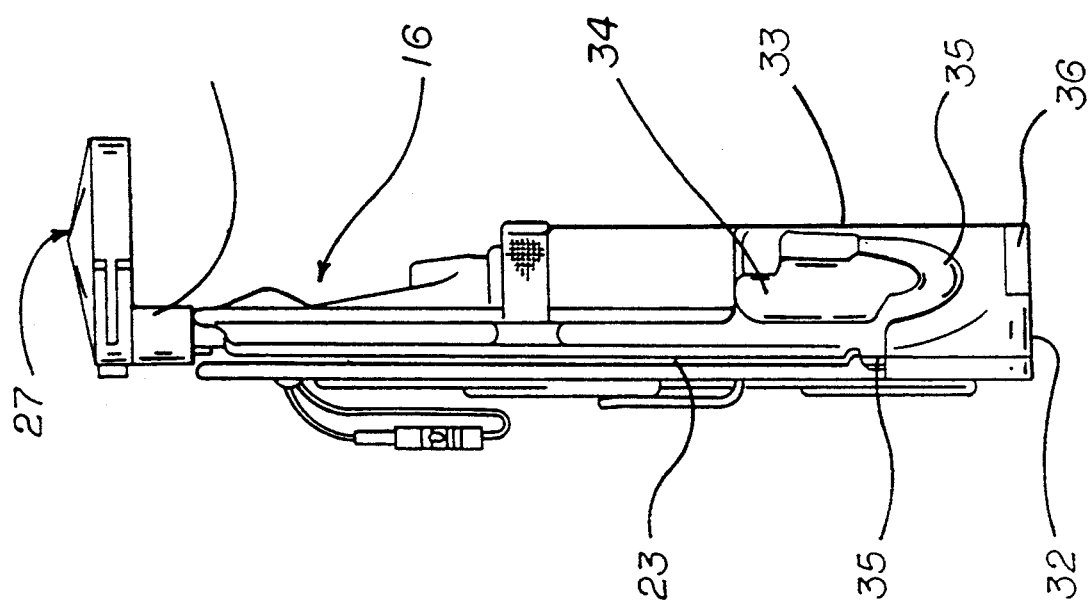

FLUID CONTAINER ATTACHMENT ADAPTOR FOR AN AMBULATORY FLUID DELIVERY SYSTEM

BACKGROUND OF THE INVENTION

1. Field of the Invention

This invention relates generally to a support device for an ambulatory fluid delivery system. More specifically, the present invention relates to an adaptor for allowing attachment of a fluid container to the support device.

2. Description of the Prior Art

It is common for patient's having certain medical problems to require periodic premeasured infusions of fluid, such as medicaments or nutrients, into their bodies. Examples of such patients are those who may require nutrients to be delivered directly into their digestive tract periodically over long periods of time, or cancer patients who require exacting amounts of medication to be delivered intravenously at precise intervals.

In the past, such patients required hospitalization for the time necessary to infuse the nutrients or medicaments, in order to allow medical personnel to perform the infusions at the proper time and in the proper amounts. Such a procedure was extremely time consuming to the patient and also the hospital personnel, and included the potential of human error in calculation of infusion dosages and injection time intervals.

An improvement on the above procedure has been to employ a programmable pump to insure that the patient receives the proper infusion dosage at the proper time period, thus relieving medical personnel from constant monitoring of the patient, and from worrying about infusion amounts and time tables. Although the programmable pump greatly relieves medical personnel of time consuming care to the patient, the patient nevertheless remained bound to the hospital bed during the prolonged infusion periods.

A further improvement has been to develop an infusion system which can not only automatically infuse preset volumes of fluid into the patient on a predetermined time table, but also allow the patient to be ambulatory. U.S. Pat. No. exemplary of portable infusion systems of this type. It discloses a fluid delivery system mounted on a portable support frame. The pump is automatically operable at selected time intervals to inject accurate amounts of fluid medication into a patient's body, and is also sufficiently compact and portable to allow the patient to be ambulatory during the infusion procedure.

Although the above described ambulatory support device of Sunderland et al. is a significant improvement in portable fluid delivery systems, there nevertheless remains a problem in its adaption to all types of fluid containers. For example, the container of a fluid delivery set may be a flexible bag, a rigid glass or plastic bottle or a burette. Although the support device of Sunderland et al. can accommodate several types of containers, there nevertheless remains room for improvement in attachment thereto of soft sided flexible bags, such as are commonly prefilled with fluid for delivery through the fluid delivery system.

OBJECTS AND SUMMARY OF THE INVENTION

Briefly, and in general terms, the present invention provides an attachment adaptor for secure an convenient attachment of a soft sided flexible fluid container of a fluid delivery set to an ambulatory fluid delivery set support device.

It is therefore an object of the present invention to provide an attachment adaptor for a portable fluid delivery system which is designed to accommodate a soft sided flexible fluid container of a standard fluid delivery set for attachment to a support device for ambulatory use.

It is another object of the present invention to provide an attachment adaptor for a support device which readily adapts the support device for use with a soft bag type fluid container of a fluid delivery set.

These and other objects and advantages of the present invention are realized in a specific preferred embodiment thereof, disclosed herein for purposes of example and not by way of limitation, which comprises an attachment adaptor for a support device, the adaptor being formed of a flat cylindrical body sized to be received within the lid clamping mechanism of the support device and including a hook member attached at a generally central position on the bottom surface of the body and extending away therefrom. The hook member is sized to be conveniently inserted into an attachment hole positioned at the top of a flexible container commonly used in fluid delivery sets in which the hole in the container has been commonly designed to allow the container to be hung on an IV pole.

Details of the structure and use of the present invention will become more apparent from the following detailed description and the accompanying drawings in which like elements are identified with like numerals throughout.

BRIEF DESCRIPTION OF THE DRAWINGS

FIG. 4 is a side view of the support device shown in FIG. 3;

FIGS. 5 and 6 show the support device of the present invention as shown in FIGS. 3 and 4 respectively, with a fluid delivery set having a flexible bag-type fluid container attached thereto for operation;

DETAILED DESCRIPTION OF THE PREFERRED EMBODIMENT

Figure 1:
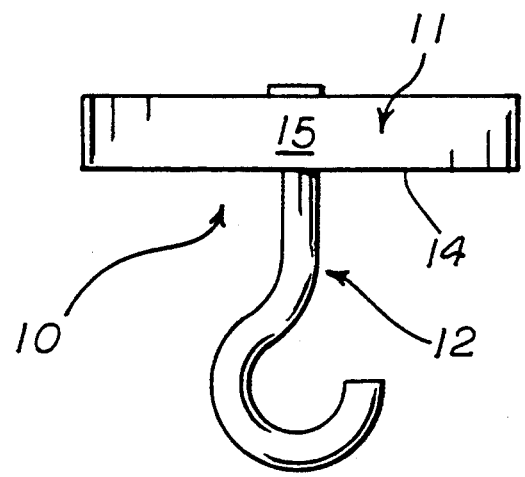
FIG. 1 is a side view of a fluid container attachment adaptor for a support device made in accordance with the principals of the present invention.
Figure 2:
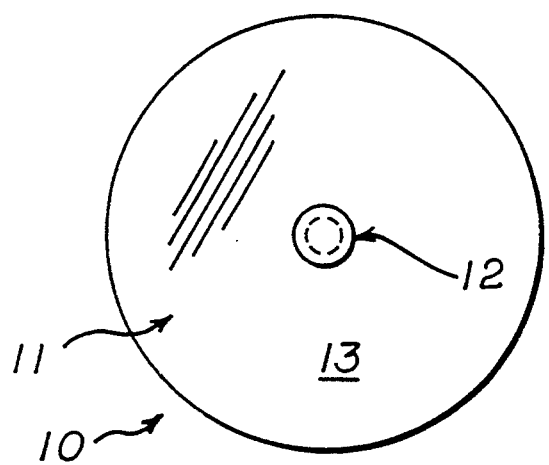
FIG. 2 is a top view of the fluid container attachment adaptor of FIG. 1.

As shown in the exemplary drawings for the purposes of illustration, an embodiment of a fluid container attachment adaptor for a support device made in accordance with the principles of the present invention, referred to generally by the reference numeral 10, is provided for convenient attachment of a soft sided flexible container of a standard fluid delivery set to an ambulatory support device therefor.

The bottle attachment adaptor 10 is preferably formed of a generally cylindrical flat disk shaped body 11. A hook member 12, preferably centrally located in the body 11, extends away from a bottom surface 14 thereof in a generally perpendicular direction. The hook member 12 may be secured to the body 11 in any well known manner, or may be formed as a integral unit with the body 11.

The hook member 12 is preferably sized to allow attachment of a IV bag thereto in the manner similar to the manner in which such IV bags are commonly attached to the hook of an IV pole.

The body 11 of the adaptor 10 may be formed of any suitable materials such as wood, plastic or metal, and the top surface 13 and bottom surface 14 thereof need not necessarily be formed flat, but may instead be formed to any desired shape in order to accommodate the clamping members of a support device. Similarly, the side surface 15 of the body 11, although shown to be formed into a cylindrical shape, may also be formed into any desired shape in order to accommodate the clamping members of a support device.

Figure 3:
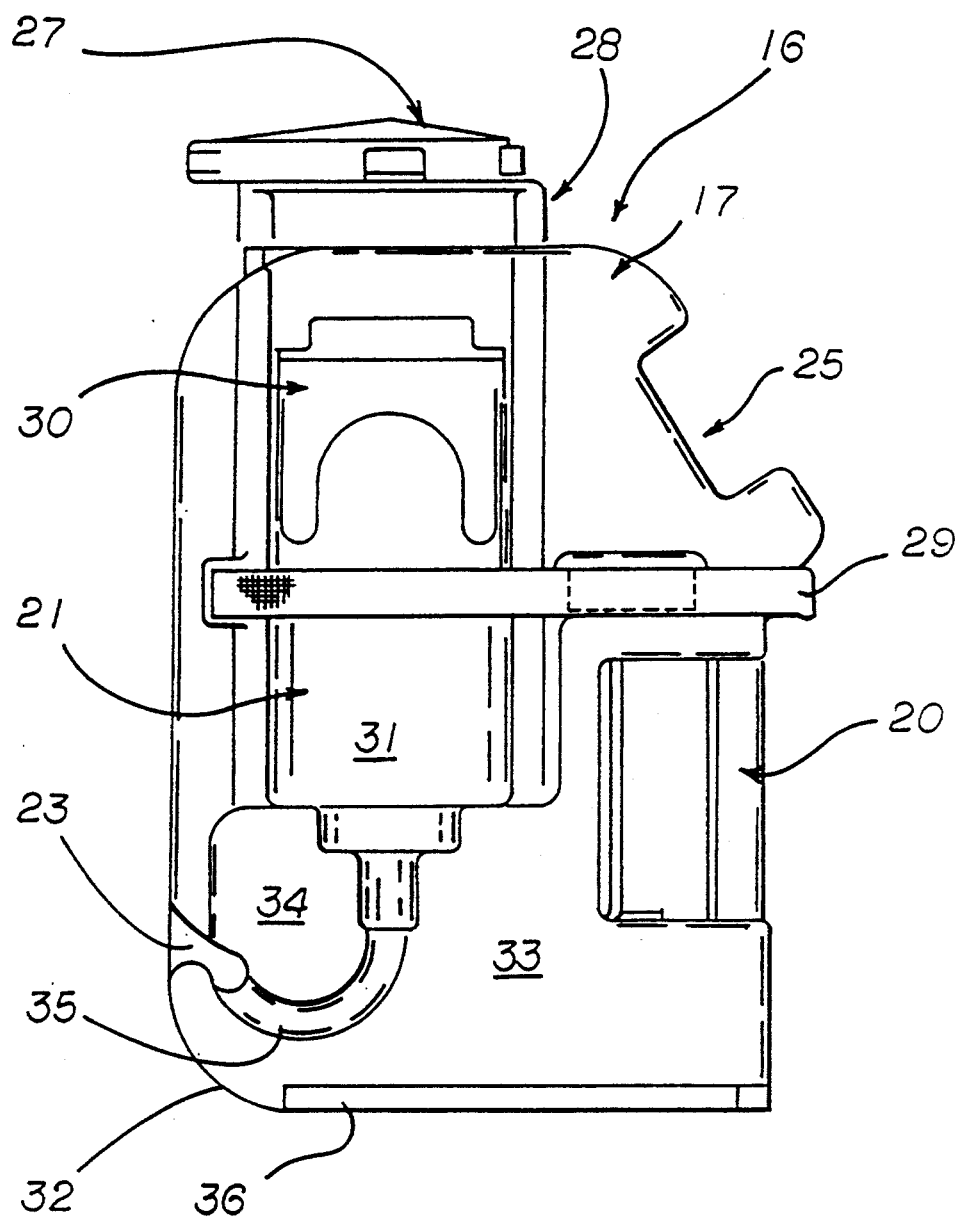
FIG. 3 is a front view of a fluid container support device usable with the fluid container attachment adaptor of the present invention.
Figure 5:
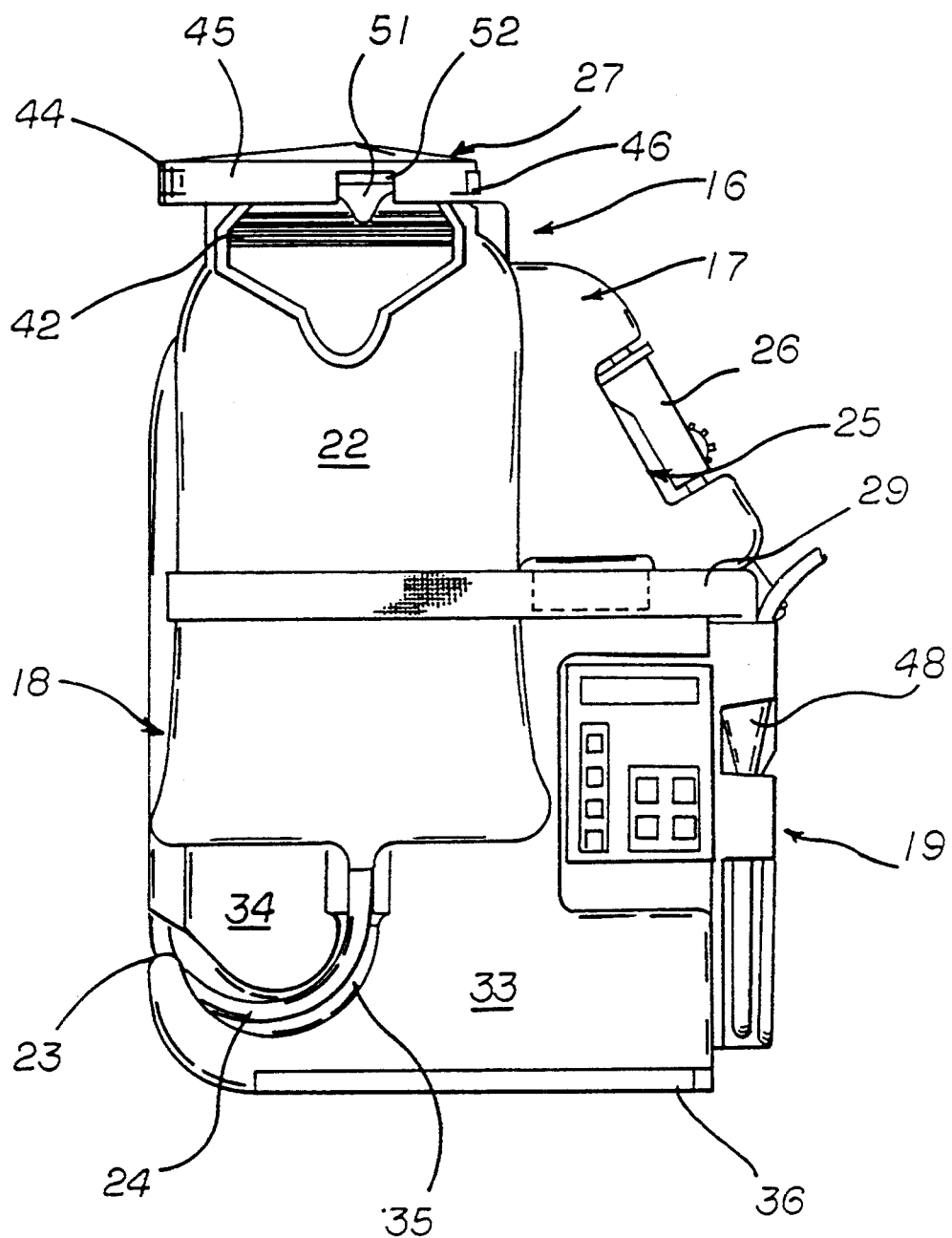
Figure 7:
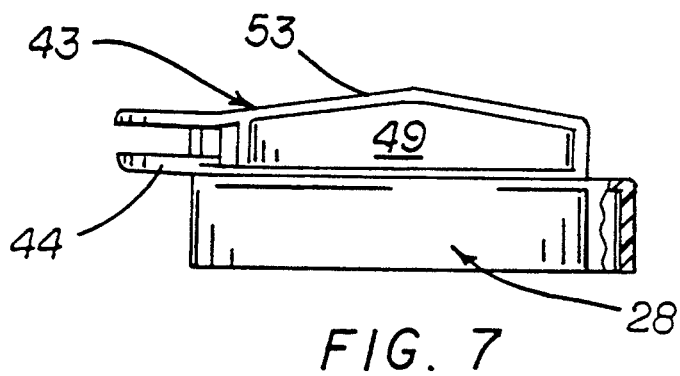
FIGS. 7-8 show the inner clamp jaw of the lid clamp of the support device.
Figure 8:
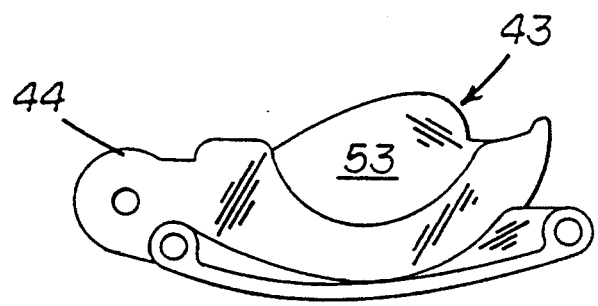
Figure 9:
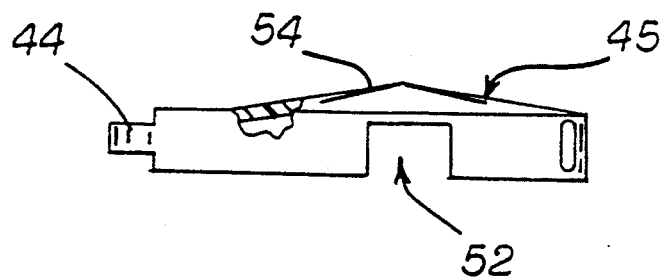
FIGS. 9-10 show the outer clamp jaw of the lid clamp of the support device.
Figure 10:
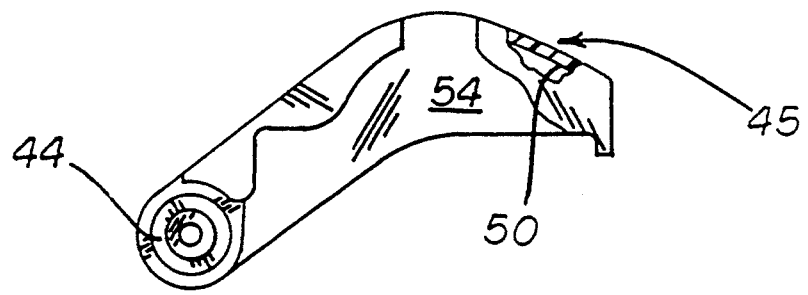

In FIGS. 3–4, an embodiment of a support device 16 operable with the present invention is shown. The device 16 includes a generally rectangular rigid body 17 which is preferably formed of a rigid plastic or other lightweight material such as wood, metal alloy, etc. Referring momentarily to FIGS. 5–6 in conjunction with FIGS. 3–4, the body 17 is adapted to receive and retain a fluid delivery set 18, which comprises a fluid container 22, a fluid delivery tube 24 with a pinch valve 26 thereon, and a drip chamber 48. An infusion pump 19 of a fluid delivery system can also be received by the support device 16.

Specifically, the body 17 forms a pump compartment 20 adapted to receive the standard infusion pump 19, a container compartment 21 adapted to partially receive a container 22 from the standard fluid delivery set 18, a tube channel 23 adapted to receive the tube 24 of the standard fluid set 18, and a valve compartment 25 adapted to receive a pinch valve 26 located on the tube 24 of the fluid set 18.

The support device 16 also includes a plurality of fastening elements which are adapted for use in securing the fluid delivery set 18 to the rigid support body 17 during use. These elements include a lid clamp 27 which is permanently affixed to a lid clamp extension 28, a securing strap 29, and a saddle bracket 30 which is secured in a flush mount position in the bottom 31 of container compartment 21.

The body 17 is also integrally formed with an elevated section 33 which forms a part of the pump compartment 20 and cooperates with a similarly elevated section 34 to form part of the tube path 35.

An extendable leg 36 may be located below elevated section 33 so as to be flush therewith when in its retracted position, and to be perpendicular therewith and parallel to base 32 when moved in to its extended position.

A more detailed description of the support device 16 is presented in U.S. patent application Ser. No. 07/819,300, filed Jan. 9, 1992, which is presently assigned to the same assignee as the present invention, and which is incorporated herein by reference in its entirety.

As best seen in FIGS. 5 and 6, the device 16 is adapted to receive the fluid set 18 which includes a soft flexible fluid bag 22 having a relatively rigid mouth and lid 42. The compartment 21 operates in conjunction with lid clamp 27 to hold the bag 22 in place. The lid clamp includes an inner jaw 43 permanently attached to the lid clamp extension 28, and attached through hinge 44 to an outer jaw 45. A fastener, such as strap 46, is attached to jaw 45 for holding it in a closed position relative to jaw 43. The strap 46 allows the clamp 27 to be securely fixed in a closed position when the lid 42 of the soft bag 22 is located therein. When in the closed position, the jaws 43 and 45 of the clamp 27 form a circular opening which hold the mouth and lid 42 of the bag 22 in place on the support device 16.

As shown in FIGS. 7–8 and FIGS. 9–10, the circular opening of the inner clamp jaw 43 forms an inner lip channel 49, and similarly, the outer clamp jaw 45 forms an outer lip channel 50 which receive the circumferential edges of mouth and lid 42 of the bag 22. Also, since the lid 42 generally includes a tab 51 thereon (see FIG. 5), the outer clamp jaw 45 is formed with a tab opening 52 through which the tab 51 can extend when the clamp 27 is closed about the lid 42.

The jaw members 43 and 45 include convex plate extensions 53 and 54 respectively which together form a generally dome-shaped surface which can effectively accommodate a bulging shape taken on by the lid 42 in the event of sudden pressurization of the bag 22 which could occur if dropped during use.

The lid clamp 27 operates to secure the lid 42 of bag 22 in its proper position and allow the bag 22 to be properly located within container compartment 21. Also the lid clamp 27 operates to prevent a sudden application of an external pressure to the bag 22 from inadvertently bursting the lid 42 open, such as may occur if the support device 16 were inadvertently dropped during use.

If desired for additional support of a container placed in container compartment 21, the strap 29 located on the front surface 37 of the body 17 can be used. The strap 29 is preferably positioned adjacent the container compartment 21 and is formed of a sufficient length to cross over the container and secure it in place.

Figure 11:
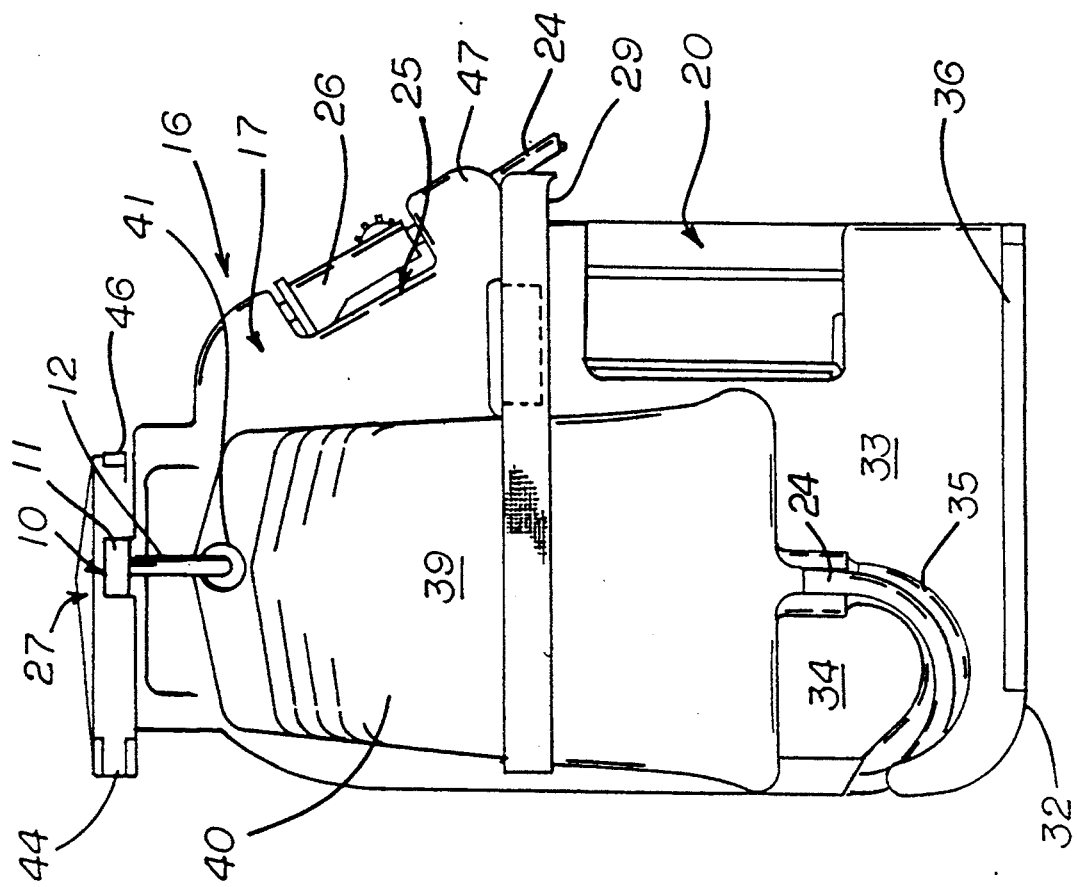
FIG. 11 is a front view of the support device including a pump and a fluid infusion set with a soft sided flexible container attached thereto for operation using the attachment adaptor of the present invention.
Figure 12:
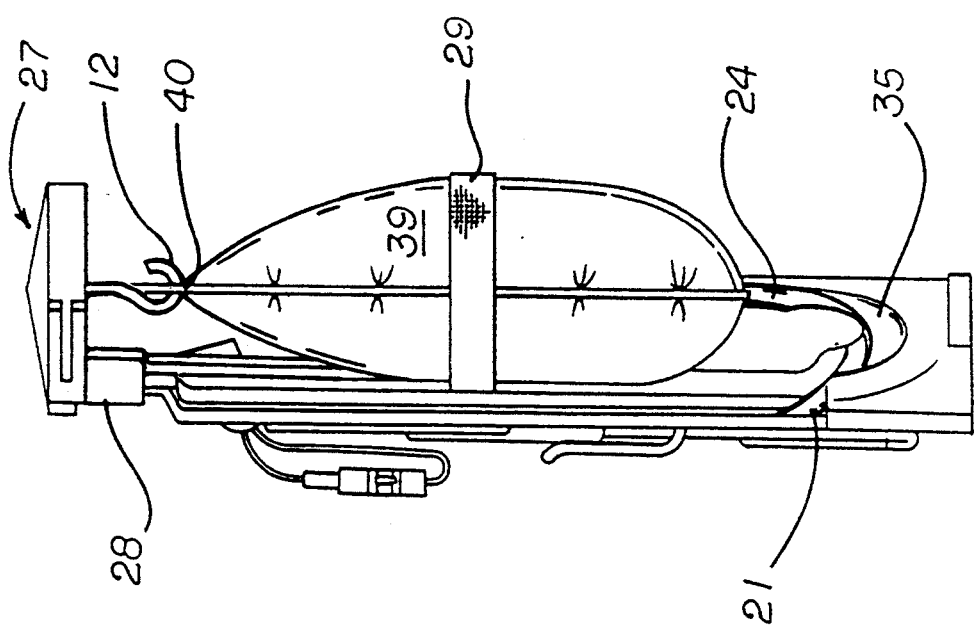
FIG. 12 is a side view of the support device and attached fluid delivery set as shown in FIG. 12.

As shown in FIGS. 11 and 12, it is often desirable to use a flexible fluid bag 39 which includes no lid. Instead, such bags are formed to include an extended edge 40 through which an opening 41 is formed to allow its attachment to the hook of an IV pole. This type of bag cannot be secured by the clamp 27 of the support device 16 as described above, without the aid of the bag attachment adaptor 10 of the present invention.

In use, as shown in .FIGS. 11 and 12, the attachment adaptor 10 is inserted into the inner lip channel 49 (see FIG. 7) of the inner clamp jaw 43, and the outer clamp jaw 45 is then closed around the adaptor 10 to allow the outer lip channel 50 (see FIG. 10) to receive the remainder of the circumferential edge of the adaptor body 11 which includes the side surface 15. It is preferable that the shape of the side surface 15 conform with, but be slightly smaller than, the shape of the inner lip channel 49 and outer lip channel 50 of the clamp when in the closed position. As shown in the present embodiment of the invention, this shape is roughly cylindrical, however, the concept of the present invention is not limited to a cylindrical shape.

Once the adaptor 10 is positioned and clamped within the clamp 27 of the support device 16, the flexible fluid bag 39 can be attached over the hook member 12 by inserting the hook member 12 through the opening 41 thereof in the manner similar to the manner in which the bag 39 would have been attached to the hook of a prior art IV pole. The strap 29 is then secured over the bag 39 to prevent its escape from the compartment 21. Next, the tube 24 is grasped and positioned within the tube path 35, then forced into the tube channel 23 and drawn the entire length of channel until pinch valve 26 is reached.

Pinch valve 26 is then adjusted along tubing 24 until it is oriented properly to be received in pinch valve compartment 25. Tubing 24 is then extended through the remainder of tubing channel 23 and allowed to extend beyond the channel exit 47.

Once the tube 24 is properly placed within the tube channel 23, it can then be attached to a pump (see FIG. 5) in the manner described in the above-identified co-pending U.S. patent application Ser. No. 07/819,300.

It will be apparent from the foregoing, while a particular embodiment of the invention has been illustrated and described, various modifications can be made thereto without departing from the spirit and scope of the present invention. Accordingly, it is not intended that the invention be limited, except as by the appended claims.

What is claimed is:

1. The combination of a fluid container attachment adaptor and a support device, said support device comprising:

means for receiving a fluid delivery set and a pump, the fluid delivery set including a fluid container and a tube for connection to the pump, said means for receiving including means for holding the pump in fixed position relative to said support device, and means for preventing kinking or occlusion of the tube, said support device also including compartment means for receiving the fluid container and clamp means, said adaptor comprising:

body means securable to said support device by said clamp means, and attachment means for securing-the fluid container to said adaptor, whereby, securing said adaptor in said clamp means of said support device and securing the fluid container to said adaptor by said attachment means, allows the fluid container to be properly positioned for operation within said support device.

2. The combination of a fluid container attachment adaptor and a support device according to claim 1 wherein said body means of said adaptor is formed in the shape of a disk, and said clamp means of said support device secures said adaptor thereto by securing said disk with said clamp means.

3. The combination according to claim 2 wherein said clamp means includes an annular channel into which at least a portion of said disk is positioned when said disk is secured by said clamp means.

* * * * *